(12) United States Patent
Zamir et al.

(10) Patent No.: US 8,865,970 B2
(45) Date of Patent: Oct. 21, 2014

(54) INDUCED HETEROSIS RELATED MUTATIONS

(75) Inventors: Dani Zamir, Gedera (IL); Zachary B. Lippman, Cold Spring Harbor, NY (US); Uri Krieger, Kibbutz Kfar HaMaccabi (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 466 days.

(21) Appl. No.: 13/122,720

(22) PCT Filed: Oct. 5, 2009

(86) PCT No.: PCT/IB2009/054348
§ 371 (c)(1),
(2), (4) Date: Jun. 6, 2011

(87) PCT Pub. No.: WO2010/041190
PCT Pub. Date: Apr. 15, 2010

(65) Prior Publication Data
US 2011/0247093 A1   Oct. 6, 2011

Related U.S. Application Data

(60) Provisional application No. 61/202,073, filed on Jan. 27, 2009, provisional application No. 61/103,048, filed on Oct. 6, 2008.

(51) Int. Cl.
*C12N 15/82* (2006.01)
*C12N 15/87* (2006.01)
*C12N 5/00* (2006.01)
*C12N 5/02* (2006.01)
*A01H 1/00* (2006.01)
*A01H 5/00* (2006.01)
*A01H 1/02* (2006.01)
*A01H 1/04* (2006.01)

(52) U.S. Cl.
CPC .. *A01H 1/02* (2013.01); *A01H 1/04* (2013.01); *C12N 15/8261* (2013.01)
USPC ........ 800/290; 800/260; 800/317.4; 800/298; 435/468; 435/430

(58) Field of Classification Search
USPC ......................................................... 800/290
See application file for complete search history.

(56) References Cited

U.S. PATENT DOCUMENTS

| 7,084,320 B2 | 8/2006 | De Block |
| 7,208,317 B2 | 4/2007 | Threadgill |
| 2009/0170712 A1 | 7/2009 | Beatty |
| 2009/0300781 A1* | 12/2009 | Bancroft et al. ................ 800/13 |

FOREIGN PATENT DOCUMENTS

| WO | 00/42838 | 7/2000 |
| WO | 03/050748 | 6/2003 |
| WO | WO 2009/021545 | * 2/2009 |

OTHER PUBLICATIONS

Lippman et al., Heterosis: revisiting the magic, 23 Trends in Genetics No. 2, 60-66 (2007).*
Lifschitz et al., Universal florigenic signals triggered by FT homologues regulate growth and flowering cycles in perennial day-neutral tomato, 57 J of Exp. Bio. No. 13, 3405-3413 at 3411 (2006).*
Redman et al., Fitness costs of jasmonic acid-induced defense in tomato, *Lycopersicon esculentum*, 126 Oecologia, 380-385 at 380-381 (2001)).*
Lifschitz et al., Universal florigenic signals triggered by FT homologues regulate growth and flowering cycles in perennial day-neutral tomato, 57 J of Exp Botany No. 13, 3405-3414 (2006).*
Lifschitz et al., The tomato FT ortholog triggers systemic signals that regulate growth and flowering and substitute for diverse environmental stimuli, 103 PNAS No. 16, 6398-6403 (2006).*
Akiyoshi, Shingo et al., (2000) A genetic linkage map of the MSM Japanese wild mouse strain with restriction landmark genomic scanning (RLGS). Mamm Genome 11(5):356-359.
Dollinger, E. J. (1985) Effects of Visible Recessive Alleles on Vigor Characteristics in a Maize Hybrid. Crop Science 25(5):819-821.
Duvick, D. N. (1999) Heterosis: Feeding people and protecting natural resources. p. 19-29 In: J.G. Coors and S. Pandey (ed.) The genetics and exploitation of heterosis in crops. Amer. Soc. Agron. Madison, WI.
Duvick, Donald N. (2001) Biotechnology in the 1930s: the development of hybrid maize. Nat Rev Gen 2(1):69-73.
Eshed, Yuval and Zamir, Dani (1995) An introgression line population of *Lycopersicon pennellii* in the cultivated tomato enables the identification and fine mapping of yield-associated QTL. Genetics 141(3):1147-1162.
Frary, A. et al., (2000) fw2.2: a quantitative trait locus key to the evolution of tomato fruit size. Science 289 (5476):85-88.
Fridman, Eyal et al., (2004) Zooming in on a quantitative trait for tomato yield using interspecific introgressions. Science 305(5691):1786-1789.
Garg, Naveen et al., (2008) Heterosis Breeding in Tomato Involving rin, nor and alc Alleles : A Review of Literature. Adv Hort Sci 22(1):54-62.
Graham, Geoffrey I. et al., (1997) Characterization of a yield quantitative trait locus on chromosome five of maize by fine mapping. Crop Science 37(5):1601-1610.
Hua, Jinping et al., (2003) Single-locus heterotic effects and dominance by dominance interactions can adequately explain the genetic basis of heterosis in an elite rice hybrid. Proc Natl Acad Sci USA 100(5):2574-2579.

(Continued)

*Primary Examiner* — Ashwin Mehta
*Assistant Examiner* — Rebecca Coobs
(74) *Attorney, Agent, or Firm* — Rodney J. Fuller; Booth Udall Fuller, PLC

(57) ABSTRACT

The present invention provides plant inbred mutant parent lines producing hybrid offspring having at least one heterosis-related phenotype, particularly total yield associated phenotypes, methods for identifying same and hybrid plants produced therefrom. The present invention further discloses heterosis-related genes and provides the corresponding isolated polynucleotides.

13 Claims, 5 Drawing Sheets

(56) References Cited

OTHER PUBLICATIONS

Kobayashi, Yasushi and Weigel, Detlef (2007) Move on up, it's time for change—mobile signals controlling photoperiod-dependent flowering. Genes Dev. 21(19):2371-84.

Kruglyak, Leonid (1999) Prospects for whole-genome linkage disequilibrium mapping of common disease genes. Nat Genet 22(2):139-144.

Kusterer, Barbara et al., (2007) Heterosis for biomass-related traits in *Arabidopsis* investigated by quantitative trait loci analysis of the triple testcross design with recombinant inbred lines. Genetics 177(3):1839-1850.

Lifschitz, Eliezer (2006) Universal florigenic signals triggered by FT homologues regulate growth and flowering cycles in perennial day-neutral tomato. J Exp Bot 57(13):3405-3414 Epub Apr. 27, 2006.

Lifschitz, Eliezer et al., (2006) The tomato FT ortholog triggers systemic signals that regulate growth and flowering and substitute for diverse environmental stimuli. Proc Natl Acad Sci USA 103(16):6398-6403 Epub Apr. 10, 2006.

Lippman, Zachary B. and Zamir Dani (2007) Heterosis: revisiting the magic. Trends in Genetics 23(12):60-6.

Luo, L. J. et al., (2001) Overdominant epistatic loci are the primary genetic basis of inbreeding depression and heterosis in rice. II. Grain yield components. Genetics 158(4):1755-1771.

Menda, Naama et al., (2004) In silico screening of a saturated mutation library of tomato. Plant Journal 38(5):861-872.

Mitchell-Olds, Thomas (1995) Interval mapping of viability loci causing heterosis in *Arabidopsis*. Genetics 140 (3):1105-1109.

Molinero-Rosales, Nuria et al., (2004) Single Flower Truss regulates the transition and maintenance of flowering in tomato. Planta 218(3):427-434 Epub Sep. 23, 2003.

Pnueli, Lilac et al., (1998) The Self-Pruning gene of tomato regulates vegetative to reproductive switching of sympodial meristems and is the ortholog of CEN and TFL1. Development 125(11):1979-1989.

Schauer, Nicolas et al., (2006) Comprehensive metabolic profiling and phenotyping of interspecific introgression lines for tomato improvement. Nat Biotechnol 24(4):447-454.

Schuler, G. D. et al., (1996) A gene map of the human genome. Science 274(5287):540-546.

Semel, Yaniv et al., (2006) Overdominant quantitative trait loci for yield and fitness in tomato. Proc Natl Acad Sci USA 103(35):12981-12986 Epub Aug. 22, 2006.

Stuber, Charles W. et al., (1992) Identification of Genetic Factors Contributing to Heterosis in a Hybrid from Two Elite Maize Inbred Lines Using Molecular Markers. Genetics 132(3):823-839.

Van Etten, W. J. et al., (1999) Radiation hybrid map of the mouse genome. Nat Genet 22(4):384-387.

Wells, Christine and Brown, Steve D. M. (2000) Genomics meets genetics: towards a mutant map of the mouse. Mamm Genome 11(7):472-477.

Xiao, Jinhua et al., (1995) Dominance is the major genetic basis of heterosis in rice as revealed by QTL analysis using molecular markers. Genetic 140(2):745-754.

Krieger et al., (2010) The flowering gene Single Flower Truss drives heterosis for yield in tomato. Nat Genet 42 (5): 459-463, and Supplementary Information pp. 1-15.

Wigge (2011) FT, a mobile developmental signal in plants. Curr Biol 21(9): R374-R378.

\* cited by examiner

INDUCED HETEROSIS RELATED MUTATIONS

RELATED APPLICATION DATA

This application is the U.S. National Stage of PCT/IB2009/054348, filed Oct. 5, 2009, which claims the benefit of U.S. Provisional Patent Application Nos. 61/202,073, filed Jan. 27, 2009, and 61/103,048, filed Oct. 6, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 8,691 byte ASCII (text) file named "Seq_List" created on Apr. 5, 2011.

FIELD OF THE INVENTION

The present invention relates to the field of plant breeding, particularly to the production of inbred parent plants providing at least one heterosis-related phenotype to a hybrid offspring, to hybrid plants produced therefrom and to genes associated with the heterosis-related phenotype.

BACKGROUND OF THE INVENTION

Heterosis, or plant hybrid vigor, is a phenomenon where hybrid plants display superior phenotypes compared to either of its inbred parent lines. Hybrid vigor was discovered in maize breeding nearly a century ago, and has subsequently been found to occur in many crop species (Duvick D N 2001. Nat Rev Gent 2, 69-74). A large portion of the dramatic increase in agricultural output during the last half of the twentieth century has been attributed to the development and use of hybrid seed varieties in core crops including, for example, corn (maize), wheat, sorghum, sunflower, alfalfa and canola.

For maize, it is estimated that heterosis increases crop yields by at least 15%, which, in combination with modern higher yielding inbred lines and improved agronomic techniques, has resulted in a steady linear increase in performance. At the end of the last century, it was estimated that 65% of maize production worldwide was hybrid-based, with other crops, such as sorghum and sunflower, showing similar numbers. Taken together, increased yield advantages due to hybrids range between 15-50%, depending on the crop (Duvick D N 1999. In: The genetics and exploitation of heterosis in crops, J G Coors and S Pandey, eds. Madison: American Society of Agronomy, Inc. and Crop Science Society of America Inc. pp. 19-29).

With such great yield benefits, it is no surprise that the breeding of food and future biofuel crops is based on developing hybrid plants; yet the principles governing heterosis are still not understood. Efforts to decipher the genetic and molecular bases of heterosis so that its power can be harnessed and utilized more efficiently have so far proven unsuccessful. Over the years, crop plants have provided the genetic resources to study heterosis because parental inbred lines have been artificially selected for maximum hybrid combining ability, and the creation of structured genetic populations allows for robust quantitative phenotyping. Indeed, much of the knowledge on heterosis comes from classic genetic studies on maize, during which the fundamental hypotheses for heterosis were defined, involving genome-wide dominance complementation as well as locus-specific, or single gene, overdominant (ODO) effects.

Attempts to refine heterosis into genetic components began a decade ago with the development of molecular markers. Subsequent quantitative trait loci (QTL) mapping in rice and maize addressed the classical models by breaking down heterosis into "Mendelian" factors and assessing their modes of inheritance (Stuber C W et al., 1992. Genetics 132, 823-839; Xiao J et al., 1995. Genetic 140, 745-754; Luo et al., 2001. Genetics 158, 1755-1771; Hua J et al., 2003. PNAS 100, 2574-2579). The evidence suggested that both dominance and overdominance (ODO) have a role in heterosis, with some involvement of epistasis, although the relative contribution of each of these mechanisms was unclear.

Little progress has been made towards the identification of genes resulting in heterotic loci, largely because of the complexity of the phenotypic interactions that define heterosis and the efforts required for QTL cloning. Despite the availability of genomic infrastructure for a wide range of plant models and suitable genetic populations, such as introgression line (IL) populations, mapping and cloning QTL with heterotic effects remains extremely challenging, and single genes causing heterosis for crop yield have still not been identified. This is primarily because most conventional QTL studies begin with the goal of mapping multiple loci for a defined phenotype, and those QTL that have been already cloned generally involve loci with significantly large effects and high heritabilities. Heterosis, in contrast, bears little similarity to previously cloned QTL as its manifestation is based on complex interactions between phenotypic components throughout development, each with its own mode of heritance, and a dynamic influence of the environment (Lippman Z B and Zamir D, TIG, 2007, 23, 60-6). This is generally referred to as "multiplicative" or "geometric" heterosis. Therefore, it can be assumed that mapping heterotic QTL is equivalent to mapping multiple, perhaps genetically unrelated traits simultaneously. This integration of traits makes the heritability of heterosis relatively low compared to more discrete phenotypes, such as fruit weight or sugar content (Frary A et al., 2000. Science 289, 85-88; Fridman et al., 2004. Science 305, 1786-1789). This complexity is highly relevant to the classic heterosis phenotype of total yield.

The cloning of heterotic genes may require additional genomic and nearly isogenic resources. Furthermore, while there are examples of chromosomal regions that may carry genes associated with heterotic yield due to pseudo-ODO (Eshed Y and Zamir D 1995. Genetics 141, 1147-1162; Graham G I et al., 1997. Crop Science 37, 1601-1610), there are no known true-ODO genes based on single gene effects. Recent data from tomato ILs provide indirect support for true-ODO (Semel Y et al., 2006. Proc Natl Acad Sci USA 103, 12981-12986). Using a phenomics approach as described above, ODO-QTL were found to be preferentially associated with traits for increased reproductive fitness, such as yield, whereas dominant, recessive and additive QTL were dispersed throughout the phenotypic categories, including non-reproductive traits. This selective association suggests that pseudo-ODO is unlikely to explain IL heterosis, as the expected overdominant-QTL for the non-reproductive traits, assuming random distribution of increasing dominant and decreasing recessive QTL throughout the genome, was higher compared to what was actually found. A heterosis study in *Arabidopsis* arrived at a similar conclusion on the basis of fewer phenotypes (Mitchell-Olds T., 1995. Genetics 140, 1105-1109).

Since heterosis is a genome-wide phenomenon, it has been speculated that its molecular mechanisms involve global changes in gene and protein expression. Recently, a comprehensive analysis on gene expression in inbreds and hybrids of B73 and Mo17 maize lines was carried out using microarrays. With nearly 14,000 genes assayed from seedling tissue, it was concluded that overdominant gene expression patterns could contribute to heterosis, acting along with all other mechanisms of gene expression, including additivity and dominance. Interestingly, a nearly identical microarray study in maize using the same parental inbred lines and hybrids came to a different conclusion where gene expression is mainly additive in heterotic hybrids, with almost no examples of ODO. The different conclusions may be the result of inherent technical issues associated with microarrays, including the source of the microarray platforms, different statistical thresholds and the like.

Mapping expression-QTL (eQTL) and analyzing the association between eQTL and phenotypic QTL has been also suggested as a tool to elucidate the molecular basis of heterosis. However, taking this approach may lead to obscured results based on the assumption that gene expression overdominance explains growth and morphological overdominance when, in fact, expression overdominance is simply one of many molecular phenotypes. It is more prudent to assume that the molecular mechanism underlying expression overdominance is independent from that of morphological phenotypic overdominance. An illustration of this concept comes from mis-expressed genes in inter-specific hybrids of *Drosophila*, which are the result of cis-trans compensatory evolution where the interaction of the trans-regulatory elements from one species with the cis-regulatory elements of the other is responsible for the dysregulation in the hybrids. Importantly, expression studies in other diploid and polyploid plants, as well as animals and yeast, using a variety of techniques show that non-additive gene expression in hybrids is a common occurrence. The fact that the majority of these studies are outside the context of heterosis suggests that there is no obvious link between global expression changes due to heterozygosity and hybrid vigor. In fact, gene expression changes in hybrids may be downstream molecular responses driven by heterotic growth effects and the genes controlling same (Schauer N et al., 2006. Nat Biotechnol 24, 447-454).

There is an ongoing attempt to develop methods and means for selecting crop plants showing heterosis using molecular and computer modeling techniques.

For example, International Patent Application Publication No. WO 00/42838 discloses methods of correlating molecular profile information with heterosis. The molecular profiling includes RNA or protein expression in a tissue of a plant, enabling the prediction of the heterosis level the plant will display if tested for a heterotic trait such as yield. That invention further discloses that selection for dominant, additive, or under/overdominant molecular profiling markers as well as selection for the number of expression products in an expression profile provides for improved heterosis. Methods of identifying and cloning nucleic acids linked to heterotic traits and for identifying parentage by consideration of expression profiles are also provided.

International Patent Application Publication No. WO 03/050748 discloses methods, computer program products, and systems for statistical analyzes of differential gene expression from hybrid offspring and their inbred parents, and the identification of genes that play a role in heterosis.

U.S. Patent Application Publication No. 2009/0170712 discloses a method for prediction of the degree of heterotic phenotypes in plants. Structural variation analyses of the genome and, in some examples, copy number variation are used to predict the degree of a heterotic phenotype in plants. In some methods copy number variation is detected using competitive genomic hybridization arrays. Methods for optimizing the arrays are also disclosed, together with kits for producing such arrays, as well as hybrid plants selected for development based on the predicted results.

U.S. Pat. No. 7,084,320 discloses methods and means for determining parent inbred plant lines with good combining ability, for determining good combinations of parent inbred plant lines capable of yielding hybrid lines with high heterosis, and further for determining the agronomical performance of different plant lines, which can be performed in vitro by determining the electron flow in the mitochondria under control and stress conditions.

However, as described hereinabove, the ability to predict and identify genes governing heterosis that can be used in crop breeding is limited, and there is an unmet need to, and would be highly advantageous to have readily defined parent inbred lines for breeding plants with hybrid vigor.

SUMMARY OF THE INVENTION

The present invention provides inbred mutant parent plant lines producing hybrid offspring having at least one heterosis-related phenotype, particularly total yield associated phenotypes. The present invention also provides methods for identifying the mutant parent plants and hybrid plants produced therefrom. The present invention further discloses heterosis-related genes and provides the corresponding isolated polynucleotides.

The present invention provides a novel approach for producing parent breeding lines that when crossed (hybridized) produce offspring showing heterosis for a desired trait, particularly traits related to total yield. Contrary to hitherto suggested methods, which are based on the attempt to correlate observed heterosis with molecular mechanisms, the present invention is based in part on the correlation of observed heterosis with induced mutations introduced on the background of an inbred parent line. Generally speaking, the methods involve observation of the desired phenotypic trait in hybrid progeny of the inbred parent and the mutants that have single induced mutation. This permits the rapid subsequent identification of the individual genes in the parent line that when mutated confer the desired heterosis related phenotype. This approach is advantageous over previously disclosed methods as each individual plant contains only one or a limited number of mutations that can be easily identified and correlated with the heterosis-related phenotype.

According to one aspect, the present invention provides a method for identifying a mutant inbred plant capable of conferring at least one heterosis-related phenotype to a hybrid offspring, comprising:

a) providing a first homozygous inbred plant population and a second homozygous mutated plant population derived from the first population having a single gene mutation and the same genetic background as of said first inbred population;

b) planting said first inbred population and said second mutated population under the same environmental conditions;

c) selecting plants from said second mutated population which show at least one phenotypic variation compared to the phenotype of said first inbred population, to obtain a selected sub-population of mutated parent inbred plants;

d) backcrossing each of the mutated parent inbred plants of the selected sub-population obtained in step (c) with a plant of said first population to produce a plurality of backcross plant populations, wherein each of the backcross populations is heterozygous solely at the mutation and homozygous in the rest of the genome;

e) screening said backcross plant populations for plants exhibiting at least one superior phenotypic trait compared to said first inbred population thus correlating individual mutated parent inbred plants with hybrid plants showing at least one superior phenotypic trait;

wherein each of said mutated parent inbred plants of step (e) confers at least one heterosis-related phenotype to a hybrid offspring.

According to alternative embodiments, backcrossing each of the mutated parent inbred plants is substituted with crossing each of the plants selected in step (c) with an independent third population of homozygous inbred plants having a distinct genetic background to produce a plurality of hybrid plant populations. Even on a distinct genetic background the heterosis related phenotype is apparent, thus confirming the relevance of the identified mutation and gene.

Methods for producing a mutated plant population, wherein the mutation is the only genetic variation compared to the genetic background of the source plant are known in the art. Typically, producing a mutated population comprises the following steps:

a) providing an inbred homozygous plant;
b) selfing the inbred homozygous plant to produce seeds; or
c) obtaining from the inbred homozygous plant parts capable of regenerating new plants;
d) inducing artificial mutagenesis in the seeds or plant parts;
e) planting the seeds or regenerating the plant parts to obtain a first generation (M1) of randomly mutated plants;
f) inbreeding (selfing) the plants of step (e) to produce M2 population segregating for the induced mutations;
g) selecting plants with a single gene mutation to produce a mutated homozygous plant population differing from the inbred homozygous plant only in the mutation site.

The selected plants are used for backcrossing to the original parental line or for crossing to a distinct parental line to establish backcross or hybrid populations for heterosis screening as described hereinabove.

Selecting plants with a single gene mutation is typically performed by scoring for one or more phenotypic alterations according to a defined set of phenotypic descriptors specific for the plant species. It is then verified that the selected mutations are the result of a mutation in a single gene through genetic progeny heritability tests in M3 generations as is known in the art.

Various methods may be use to induce artificial mutagenesis in the seeds or plant parts. According to certain embodiments, mutagenesis is induced by a method selected from the group consisting of chemical treatment with a mutagenizing compound, including, for example, ethyl methane sulfonate (EMS); irradiation with X-ray; UV irradiation; fast neutron irradiation; T-DNA or transposon insertion; and combinations thereof.

In plant populations, phenotypic variation is the result of genetic variability as well as of environmental conditions under which the plants are grown. Thus, populations compared for phenotypic variation according to the methods of the present invention are grown under the same environmental conditions, such that the observed phenotypic change is due solely to the genetic variation when compared to the original non-mutagenized parental lines. Typically, the compared populations are grown in agricultural greenhouse and/or field trial in multiple environment conditions and plant densities to reveal as many phenotypic changes as possible. As the compared populations have the same genetic background except a single mutation, the phenotypic variation(s) can be directly attributed to that mutation, which is confirmed through M3 heritability progeny tests.

Homozygous mutant plants showing any phenotypic variation compared to the isogenic plants of the first inbred population are selected for further crossing (step c), regardless of the nature of the phenotypic variation. It is to be explicitly understood that the phenotype may be superior or inferior in terms of plant growth, yield etc. Surprisingly, the present invention now discloses particular mutations that, when in a homozygous form result in reduced gene function or loss of gene function that causes individual or multiple, often deleterious, changes to plant growth, morphology, and yield; however, when in a heterozygous form the mutation confer heterosis on the hybrid plant, particularly heterosis for yield. Thus, according to typical embodiments, homozygous mutant plants showing inferior phenotypic alterations compared to the non-mutant plant are selected.

Plants of the backcross or hybrid populations, which are heterozygous for the single gene mutation, are selected only for a superior phenotypic trait compared to the first population phenotype.

According to certain typical embodiments, the superior phenotypic variation is associated with yield-affecting traits. According to certain embodiments, the yield-affecting traits having a direct or indirect effect on the yield are selected from the group consisting of vegetative growth rate, plant weight, flowering time, inflorescence number, number of flowers per inflorescence, timing of fruit or grain set, fruit or grain weight, tolerance to biotic stress, including tolerance to pathogens and tolerance to abiotic stress, including heat, cold, drought and the like.

The methods of the present invention can be performed with any crop or plant that its seeds or regenerable parts may be mutagenized, and, preferably, a plant that may be easily screened for phenotypic mutations. According to certain embodiments, the plant is a crop plant. According to other embodiments, the plant is a dicotyledonous plant selected from the group consisting of tomato, pepper, and soybean. According to additional embodiments, the plant is monocotyledonous plant selected from the group consisting of maize, rice, wheat, and barley. According to further embodiments, the plants are ornamental plants or crop trees.

According to certain aspects of the present invention, the mutation associated with heterosis when in heterozygous form is genetically mapped according to standard techniques and the specific alteration in the DNA of the single gene mutation is identified. According to these aspects, the method for identifying the mutant parent inbred line further comprises mapping the genomes of plants of the backcross or hybrid populations exhibiting at least one superior phenotypic trait, or their mutant parent inbred plant, whereby a genetic locus that modulates the phenotype is identified.

Any method as is known in the art for mapping and cloning the mutated gene or fragment thereof can be used with the teachings of the present invention. Mapping can comprise, for example, analyzing genetic polymorphisms segregating in the backcross population, linkage analysis, linkage disequilibrium analysis, restriction landmark genomic scanning (RLGS) and radiation hybrid.

Isolated polynucleotides comprising heterosis-associated mutations are also provided by the present invention.

According to certain aspects, the present invention provides an isolated polynucleotide encoding a mutated sft protein having the amino acid sequence set forth in SEQ ID NO:3. According to certain embodiments, the polynucleotide comprises the nucleic acid sequence set forth in SEQ ID NO:4.

According to another aspect, the present invention provides a mutant parent inbred plant identified by the method of the present invention, the mutant parent inbred line conferring at least one heterosis-related phenotype to a hybrid offspring.

According to certain embodiments, the parent inbred line is homozygous for the mutant sft gene comprising the nucleic acid sequence set forth in SEQ ID NO:4.

According to a further aspect, the present invention provides a method for producing hybrid plant showing at least one heterotic phenotype, comprising:
  a) providing a mutant parent inbred plant identified by the method of the present invention homozygous for a single mutation in a single gene;
  b) providing a non-mutant parent inbred plant, homozygous for wild type copies of the gene; and
  c) crossing (hybridizing) the mutant parent inbred line with the non-mutant parent plant;
thereby producing heterozygous hybrid plants showing at least one heterotic phenotype that is superior compared to the phenotypic performance of at least one of the parent plants.

According to certain embodiments, the hybrid plant shows at least one heterotic phenotype that is superior compared to the phenotypic performance of the best parent plant.

According to certain embodiments, the heterotic phenotype is yield-related. According to other embodiments, the hybrid plant shows heterotic phenotypes compared to the non-mutant inbred parent plant. Said heterotic phenotypes can result from one or multiple phenotypic characters altered in the heterozygous plant.

According to other embodiments, the non-mutant inbred parent plant is isogenic to the mutant parent plant. As used herein, the term "isogenic to the mutant parent plant" refers to a plant having the same genetic background except for the single gene mutation. According to other embodiments, the mutant parent line is essentially homozygous.

It is to be explicitly understood that plants comprising more than single mutation, each of which identified by the methods of the present invention, are also encompassed in the scope of the present invention. Combining mutations (pyramiding) is well known to a person skilled in the art. Accordingly, hybrid plants showing at least one heterotic phenotype that is superior compared to the phenotypic performance of at least one of the parent plants produced by the method described above, comprising more than a single mutation, are also encompassed within the scope of the present invention.

According to certain embodiment, the gene is tomato SINGLE FLOWER TRUSS (SFT) gene or an ortholog thereof. According to these embodiments, the heterozygous hybrid plant comprises a structurally intact and functional wild-type SFT gene copy and a mutated sft copy, wherein the mutation in the sft copy is such that it reduces SFT gene function when homozygous; said heterozygous plant features a quantitative heterosis in respect to at least one yield-related parameter as compared to a homozygous plant having two functional wild-type copies of the SFT gene.

According to certain embodiments, the wild type SFT gene encodes a protein having the amino acid sequence set forth in SEQ ID NO:1. According to one embodiment, the wild type SFT gene comprises a nucleic acid sequence as set forth in SEQ ID NO:2.

According to other embodiments, the mutated sft gene encodes a protein having the amino acid sequence set for the in SEQ ID NO:3. According to one embodiment, the gene comprises a nucleic acid sequence as set forth in SEQ ID NO:4.

According to further embodiments, the mutated sft gene encodes a protein having the amino acid sequence set for the in SEQ ID NO:5. According to one embodiment, the gene comprises a nucleic acid sequence as set forth in SEQ ID NO:6.

According to yet additional embodiments the mutated sft gene encodes a protein having the amino acid sequence set for the in SEQ ID NO:7. According to one embodiment, the gene comprises a nucleic acid sequence as ser forth in SEQ ID NO:8.

According to certain embodiments, the plant is tomato plant (*Solanum lycopersicum*). According to other embodiments, the plant is a crop plant other than tomato and the gene is an ortholog of the SFT gene.

Hybrid plants produced by the method of the present invention are also encompassed within the scope of the present invention.

According to certain embodiments, the present invention provides a heterozygous hybrid plant comprising a structurally intact and functional wild-type SFT gene copy and a mutant sft copy, wherein the mutation in the sft copy is such that it reduces SFT gene function when homozygous; wherein the heterozygous plant shows a quantitative heterosis in respect to at least one yield related parameter as compared to a homozygous plant having two functional wild-type copies of the SFT gene.

According to certain typical embodiments, the present invention provide a hybrid plant heterozygous for the SFT gene, comprising a wild type SFT gene having the nucleic acid sequence set forth in SEQ ID NO:2 and a mutant sft gene having a nucleic acid sequence selected from the group consisting of SEQ ID NO:4, SEQ ID NO:6 and SEQ ID NO:8, wherein the hybrid plant has increased yield compared to a plant selected from the group consisting of a plant homozygous for the SFT gene and a plant homozygous for the sft gene. According to additional typical embodiments, the mutant sft gene comprises the nucleic acids sequence set forth in SEQ ID NO:4

Other objects, features and advantages of the present invention will become clear from the following description and drawings.

DETAILED DESCRIPTION OF THE INVENTION

Figure 1:
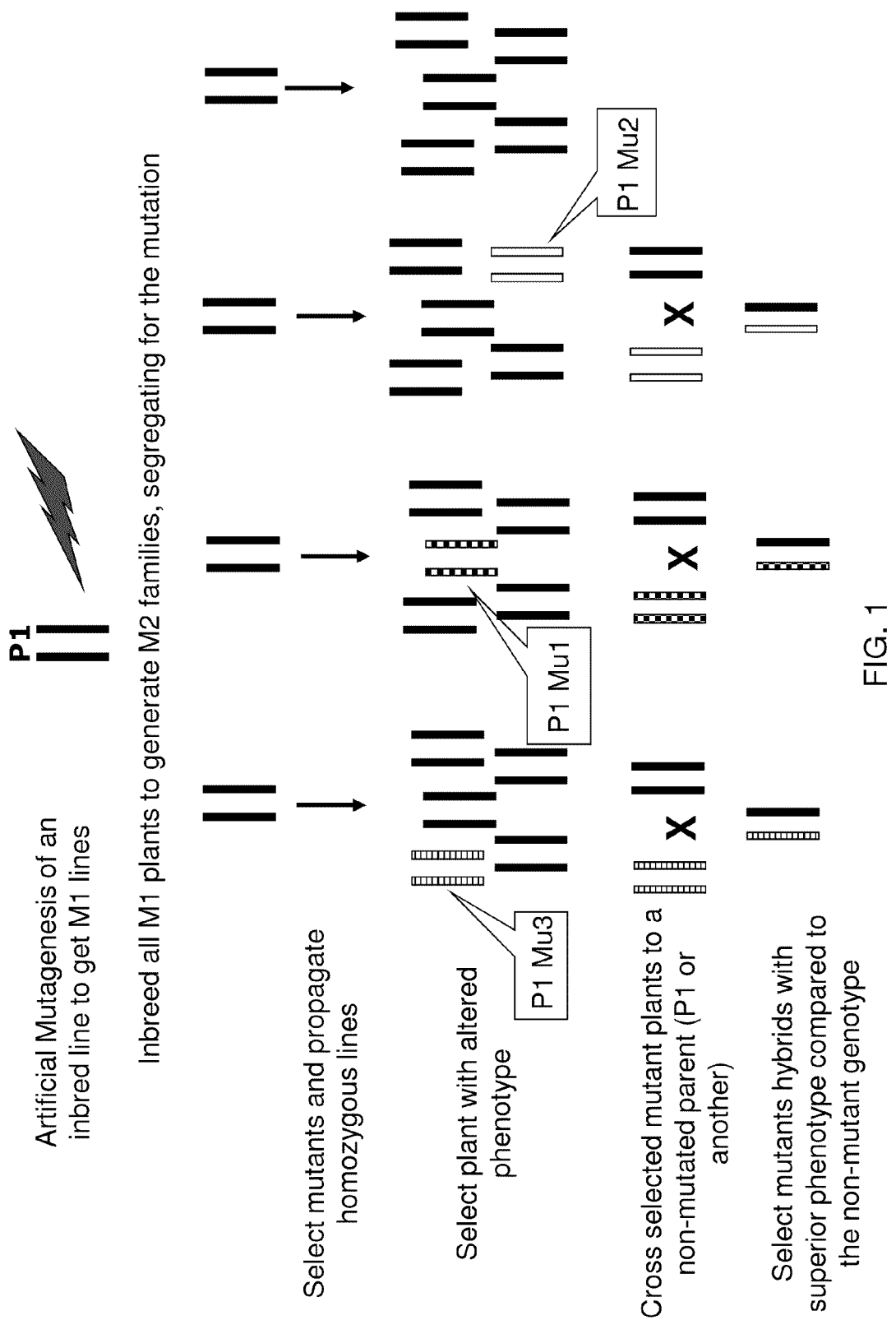
FIG. 1 shows schematic illustration of the method for identifying mutant inbred plants conferring at least one heterosis related phenotype to its hybrid offspring.

The present invention addresses the ongoing need for tools for producing improved agricultural crops. Particularly, the present invention provides methods for linking a particular mutation with heterosis. These mutations are used to produce hybrid plants having improved plant vigor, particularly plants having improved yield parameters.

DEFINITIONS

The term "plant" is used herein in its broadest sense. It includes, but is not limited to, any species of woody, herbaceous, perennial or annual plant. It also refers to a plurality of plant cells that are largely differentiated into a structure that is present at any stage of a plant's development. Such structures include, but are not limited to, a root, stem, shoot, leaf, flower, petal, fruit, etc.

The terms "heterosis" and "plant vigor" are used herein in their common meaning as is known in the art, referring to increased vigor or other superior qualities arising from the crossbreeding of genetically different plants. "Heterosis-related phenotype" means an observable trait in a plant where the phenotype exhibited in hybrid plants is more desirable when compared to the corresponding phenotype exhibited in homozygous parent plants.

As used herein, the term "phenotype" generally refers to any observable character or property of a plant. The observable property depends upon the genome of the organism, and can be further characterized as modulated by a non-genetic factor, an interaction between two or more non-genetic factors, an interaction between a genetic locus and a non-genetic factor, or an interaction between two or more genetic loci and non-genetic factors. A non-genetic factor comprises an environmental condition or exposure, for example growth conditions, biotic and abiotic stresses. The term "trait" as used herein refers to a characteristic phenotype.

As used herein, the terms "parent plant lines" or "parent plants" refers to open and closed pollinated, inbred lines, stable for the desired traits over cycles of self-pollination and planting. The term "hybrid plant" refers to plant that result from a cross between genetically different individuals, typically two distinct parent lines.

The terms "first" and "second", for example, as used herein to describe various plant populations are included for clarity of description and are not meant to be limiting.

The terms "mutating" and "mutagenizing" are used herein interchangeably to refer to a method for inducing one or more genetic modifications in cellular nucleic acid material. The term "mutation" as used herein refers to any alteration of DNA to a form that is different compared to its naturally occurring form. Representative gene modifications include nucleotide insertions, deletions, substitutions, and combinations thereof, and can be as small as a single base or as large as tens of thousands of bases.

The terms "mapping" and "gene mapping" are used interchangeably to refer to progressive resolution of genomic sequence conferring a phenotype. A typical mapping experiment employs linkage analysis of a target locus and genetic polymorphisms. The results of a mapping method can be expressed as map units or centimorgans.

The term "polymorphism" refers to the occurrence of two or more genetically determined alternative sequences or alleles in a population. An allelic difference can be as small as one base pair.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

As used herein, the term "allele" refers to one member of a pair or series of genes that occupy a specific position on a specific chromosome.

As used herein, the term "functional copy" refers to the wild type gene present in heterozygous form in the heterotic hybrid plants of the invention. According to certain embodiments, this term refers to the tomato wild type and functional SFT gene having the nucleic acid sequence ser forth in SEQ ID NO:2.

The term "reduction of SFT gene function" as used herein refers to a mutation in the SFT gene that when present in homozygous form causes unfavorable flowering and plant architecture due to the poor flower/fruit production and a large bushy plant habit resulting from the "indeterminate" vegetative inflorescences that inhibit the reiteration of vegetative leaf-producing shoot and floral flower-producing shoot (sympodial) units.

As used herein, the term "ortholog" refers to any gene found in two or more species that can be traced to a common ancestor.

As used herein, the term "dominant" expression for an expression product (i.e. a polynucleotide or polypeptide) refers to the situation where expression of the product in a progeny differs from one parent, but does not differ from the second parent. The term "additive expression" for an expression product refers to the situation where expression of the product in a progeny falls within the range of the two parents (and may or may not differ significantly from both parents). The terms "overdominant" or "overdominance" are used herein interchangeably and refer to the situation where expression of an expression product in a progeny differs from both parents and falls outside of the range of the two parents over the higher parent value. Further, the term "differ" when referring to values is dependent on the technologies being utilized and is defined within the detection limits of such technologies.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

An "isolated" nucleic acid molecule is one that is substantially separated from other nucleic acid molecules which are present in the natural source of the nucleic acid (i.e., sequences encoding other polypeptides). Preferably, an "isolated" nucleic acid is free of some of the sequences which naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by agro-infection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

PREFERRED MODES FOR CARRYING OUT THE INVENTION

Hybrid vigor, or heterosis, of heterozygous plants had been described by Darwin. The first practical and intellectual exploration into heterosis commenced in the beginning of the $20^{th}$ century by the discovery that inter-crossing different poor-yielding inbred varieties of maize produced hybrids with superior growth and yield. It took an additional 25 years until the first commercial double cross hybrids were marketed, and a few more years after that until inbred lines became vigorous enough to produce sufficient amount of seeds. At that point, superior single-cross hybrid seeds started dominating the corn seeds market, demonstrating the power of heterosis. The success of F1 hybrid production has increased food production in many regions of the world and dramatically increased yield from 15 to 50%, depending on the crop (Duvick D N., 2001. ibid).

Heterosis is a quantitative trait with a complex mode of inheritance due to its effect on multiple developmental processes. Crop plants have been the primary models in attempts to break down heterosis into genetically tractable components, because parental inbreds have been selected for maximum heterotic combining ability, and the creation of controlled genetic populations has allowed for robust quantitative phenotyping. The greatest challenge in heterosis research centers on identifying the genes that drive the process, and unequivocally establishing a direct association between heterotic phenotypes and the molecular factors underlying them.

The present invention discloses a novel approach for identifying heterosis-related genes, based on the production of a mutated population of plants and attributing a certain mutation to heterotic phenotype when a mutation is in the heterozygous state. Moreover, the present invention now discloses that mutations having negative effects on the plant when in homozygous form may confer heterosis when in heterozygous form, particularly on traits that affect, directly or indirectly, the total yield.

Thus, according to one aspect, the present invention provides a method for identifying a mutant parent inbred plant conferring at least one heterosis-related phenotype to a hybrid offspring.

The principles of the method of the invention are illustrated schematically in FIG. 1. The first step of the method of the invention relies on starting material of inbred homogenous plants of a given species. This parental line is chosen as the genetic foundation for an induced artificial mutagenesis, such as through chemical treatment with compounds such as ethyl methane sulfonate (EMS), irradiation with X-ray, UV irradiation, fast neutron irradiation, or T-DNA or transposon insertion. Mutations can be induced in any plant part that can be regenerated to a whole plant. Typically, mutations are induced in the seeds of plants. In certain crops, haploid or diploid pollen may serve as the started material for a mutated plant population. Alternatively, plant tissue cultures are exposed to the induction of mutations. The mutated plant parts are used to generate a series of first generation (M1) randomly mutated plants. Mutated plants M1 are inbred that then give rise to progeny (M2) plants where individual mutants can be identified in segregating populations.

A screen for mutants and selection of plants showing a change in one or more phenotypic characters that distinguish them from the parental line is then performed. Traits associated with yield are particularly followed, but the screening and selection is not restricted to such traits. Importantly, these changes in character need not be related to, or affect, yield components directly. Mutant screening can be performed when the plants are grown under greenhouse or field conditions. The population of the selected mutated plants, or the "mutation library", is then used to identify heterosis-related mutations. It is to be explicitly understood that at this stage, plants showing any phenotypic change compared to the non-mutated parental plants are selected. Surprisingly, the present invention now discloses that deleterious phenotypes, particularly of reduced productivity, observed in mutated plant homozygous for the mutation, are converted to superior heterotic phenotypes when the plant is heterozygous to the same mutation.

The method of the present invention can be employed using known mutation libraries, for example the isogenic tomato mutation library in the genetic background of the inbred M82 described in the Example section hereinbelow. Additionally or alternatively, new mutation libraries can be produced as described hereinabove.

According to certain embodiments, the mutagenizing methods employed according to the teachings of the present invention are substantially random such that a genetic modification can occur at any available nucleotide position within the nucleic acid material to be mutagenized, i.e. there is no preference or increased frequency of occurrence of mutagenesis at particular nucleotide sequences.

Any mutagenic agent as is known in the art can be use, including, but not limited to ultraviolet light, X-ray radiation, gamma radiation, N-ethyl-N-nitrosourea (ENU), methyinitrosourea (MNU), procarbazine (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C (MMC), N-methyl-N'-nitro-N-nitrosoguanidine (MNNG), $^3H^2O$, and urethane (UR). *Agrobacterium*-mediated Transfer-DNA (T-DNA) or transposon insertion can be also used.

The frequency of genetic modification upon exposure to one or more mutagenic agents can be modulated by varying dose and/or repetition of treatment, and can be tailored for a particular application/plant species. For example, if subsequent phenotypic screening involves identification of a rare phenotype, then a frequency of genetic modification can be selected whereby multiple mutations are induced on each chromosome. Similarly, if the library will be used to screen for a more general differentiation phenotype, then the dose and administration of mutagen can be varied to generate a relatively fewer number of genetic modifications per chromosome. In one embodiment, the treatment dose and regimen does not induce substantial cytotoxicity.

According to certain embodiments, yield-affecting traits having a direct effect on the yield are selected from the group consisting of, but not limited to, vegetative growth rate, plant weight, flowering time, inflorescence number, number of flowers per inflorescence, timing of fruit or grain set and fruit or grain weight. According to other embodiments, the yield-affecting traits having indirect effect on the yield are selected from the group consisting of tolerance to biotic stress, including tolerance to pathogens and tolerance to abiotic stress, including heat, cold, drought and the like.

Mutants of single or multiple random phenotypic classes representing inherited mutations of single genes showing altered phenotype as described above are selected by identifying one or more phenotypic alterations according to a defined set of phenotypic plant-species specific descriptors, to then verify that selected mutations are the result of a mutation in a single gene through genetic progeny heritability tests in M3 generations and subsequently backcrossed to the original non-mutagenized parent to generate "mutant hybrid" seed. This seed carries one mutated copy of a gene and one functional copy of the same gene in the corresponding genomic (i.e. allelic) position, thereby making it heterozygous for the mutation. The remaining sets of genes and intergenic chromosomal segments are homozygous. Alternatively, the selected mutated plant is crossed with an unrelated inbred parent. The produced seed progeny is heterozygous for the mutation and heterozygous for the remaining sets of genes in a traditional hybrid sense. Several mutations identified according to the teachings of the present invention may be combined into one mutant parent plant. In this case, the produced hybrid seed progeny will be heterozygous for each of the mutation.

The mutant hybrid seeds are then tested in agricultural greenhouse and/or field trials in multiple environments and planting densities and are compared directly to the homozygous parental line not carrying a mutated copy of the gene. Desired traits (such as for example yield-related traits) are measured in a comprehensive replicated and randomized manner and appropriate statistical analyses are performed to determine significant changes in phenotypic traits. Mutant hybrids that show heterosis are selected for further evaluation, including evaluation of additional traits, particularly yield-related traits, and under additional environmental conditions. Hybrids that maintain the heterotic phenotype for the desired trait(s) comprise a heterosis-related mutation. The parental homozygous mutated inbred plants of these hybrids are the source for the heterosis-related mutation, and they are indentified within the original mutated population.

The mutant parent inbred plants identified according to the teachings of the present invention, which confer at least one heterosis-related phenotype to their hybrid offspring, can be used for the commercial production of the desired hybrid plant without the need to identify the specific heterosis-related mutation.

Nevertheless, according to certain aspects of the invention, the heterosis-related mutations are identified. According to certain embodiments, the mutations are mapped and cloned.

Techniques for gene mapping are well known to one skilled in the art, including linkage analysis (e.g., Wells C and Brown S D., 2000. Mamm Genome 11, 472-477), linkage disequilibrium analysis (Kruglyak L., 1999 Nat Genet 22, 139-144), restriction landmark genomic scanning (RLGS) (Akiyoshi S et al., 2000. Mamm Genome 11, 356-359), and radiation hybrid mapping (Schuler G D et al., 1996. Science 274, 540-546; Van Etten W J et al., 1999. Nat Genet 22, 384-387).

Any suitable mapping technique can be used, and it will be appreciated by one of skill in the art that no particular choice is essential to or a limitation of the presently claimed subject matter.

According to these aspects, the present invention provides mutations in tomato SFT gene that reduce its function when homozygous, and quantitatively modulate heterosis for yield when in the presence of a functional copy of the SFT gene in a heterozygous form. The invention further provides mutated orthologs of the SFT gene of other crop species that can modulate heterosis for yield when present in the heterozygous condition.

The growth processes of plants depend on the concurrent action of environmental cues and innate responses. In flowering plants, termed angiosperms, the induction of flowering marks a major transition from vegetative to reproductive growth, resulting in flower, fruit, and seed development. This developmental shift, which is a major determinant of reproductive success and crop yield potential, is primarily triggered by changes in day length, which is known as photoperiodism. Flowering in many species is a consequence of either short-days or long-days, and some species are day-neutral (Thomas B and Vince-Prue D., 1997. In: Photoperiodism in plants. New York: Academic Press). Regardless of which class a plant falls under, innate internal responses lead to changes in cell differentiation among groups of pluripotent stem cells of the apical meristems that give rise to all plant organs. Studies aimed at deciphering the molecular mechanisms responsible for the shift from a vegetative to a reproductive meristem have lead to the identification of a mobile molecule named "florigen", which is produced in the leaves under inductive photoperiods and translocated to shoot apical meristems (SAMs) to induce flowering.

Genetic and molecular studies in *Arabidopsis*, which is a facultative long-day plant, showed that mutants in a gene called FLOWERING LOCUS T (FT) were late-flowering and were targets of a gene called CONSTANS (CO), which is under the influence of the circadian clock. However, while CO was originally suggested to be florigen, its ability to induce flowering was not universal.

Independent studies in *Arabidopsis*, rice, and tomato have since revealed that FT and its orthologs in other species function as the mobile flowering signal. Direct evidence implicating FT as a major genetic and molecular component of florigen came from tomato, where it was shown that overexpression of the FT ortholog, SINGLE FLOWER TRUSS (SFT), could induce flowering in tomato sft mutants and furthermore, could induce flowering when present as a heterologous gene in a late flowering cultivar of tobacco (Kobayashi Y and Weigel D., Genes Dev. 2007. 21(19), 2371-84).

Further studies showed that FT and its orthologs have dramatic and universal effects on flowering time, which in turn, regulates plant architecture, and other agronomically important traits directly related to yield in crop plants. For example, in tomato, sft mutants are late flowering and alter the reiterated compound growth pattern of the tomato plant, which provides the foundation for yield (Lifschitz E and Eshed Y., 2006. J Exp Bot 57, 3405-3414). Tomato, like all members of the Solanaceae family, produces a compound "sympodial" shoot system by cycling between growth termination and renewal of SAMs, such that tomato growth is modular and undergoes numerous vegetative to floral transitions during growth, resulting in a plant composed of hundreds of branches, inflorescences, and flowers. Essentially, flowering and fruit production in tomato is based on the genetic regulation of two flowering events—the number of leaves generated until the primary inflorescence is formed on the primary and axillary shoots, and the number of leaves between the inflorescences borne out of sympodial growth.

Two major genes have been found to regulate sympodial growth in tomato. The first is SELF PRUNING (SP), which is an ortholog of TERMINAL FLOWER 1 (TFL1) from *Arabidopsis* and CENTRORADIALIS (CEN) in *Antirrhinum*. The normal function of SP is to repress flowering. Thus, sp mutants flower more rapidly, which causes a progressive reduction in the number of leaves within sympodial units such that the plant eventually terminates with two consecutive inflorescences (Pnueli L et al., 1998. Development 125, 1979-1989).

SFT was the second gene found to have a major impact on sympodial shoot growth, because sft mutants, in addition to being late flowering, transform the normal tomato compound inflorescence into an ever-growing indeterminate vegetative shoot where single flowers are separated in space by leaves (Lifschitz F et al., 2006. Proc Natl Acad Sci USA 103, 6398-6403). This indeterminacy prevents the release of the first sympodial shoot through a failure to release apical dominance, thereby precluding the production of reiterated sympodial units.

At least four independent sft mutations have been identified and used to clone the SFT gene. Interestingly, SFT was found to be a member of the same gene family as SP/TFL1/CEN. These gene products are all related to a phosphatidylethanolamine binding protein that may be a component of membrane complexes involved in signal transduction or a transcriptional co-activator.

As a crop plant, tomato has been bred to have beneficial agronomic traits, especially those phenotypes relating to flowering time, plant architecture, fruit production and fruit size. In fact, the sp mutation has become the most important genetic change in the development of processing tomato varieties, because the "determinate" growth habit conferred by the sp mutation facilitates mechanical harvest and the breeding of uniform fruit ripening (Pnueli et al., 1998. ibid). In contrast, homozygous mutants of sft have a negative impact on flowering and plant architecture due to the poor flower/fruit production and bushy plant habit resulting from the indeterminate vegetative inflorescences that inhibit the reiteration of sympodial units. Thus, the four known mutations of sft have been studied strictly from a developmental perspective, highlighting the role of SFT in flowering time and related developmental processes (Lifschitz and Eshed, 2006. ibid; Lifschitz et al., 2006. ibid).

Surprisingly, employing the method of the present invention for identifying mutant plants that induce heterosis with a tomato mutation library, it is now disclosed that tomato plants heterozygous for a mutation in the SFT gene show increased yield through single-gene heterosis.

Three independent mutations of sft that can cause single gene heterosis were identified. sft-4537, comprising the nucleic acid sequence set forth in SEQ ID NO:6, encoding a protein having the amino acid sequence set forth in SEQ ID NO:5; sft-7187, comprising the nucleic acid sequence set forth in SEQ ID NO:8, encoding a protein having the amino acid sequence set forth in SEQ ID NO:7; and sft-stop, comprising the nucleic acid sequence set forth in SEQ ID NO:4, encoding a protein having the amino acid sequence set forth in SEQ ID NO:3.

The mutation in sft-4537 is a single base-pair change at nucleotide position 194 (from c to t) that results in a single amino acid change from Threonine (T) to Isoleucine (I).

The mutation in sft-7187 is a two base-pair deletion at positions 466-467 of the wild type SFT gene (SEQ ID NO:2) that causes a frame shift and a downstream stop codon that truncates the C-terminus of the SFT protein.

These two mutations were previously described in a publication utilizing homozygous sft mutants that flowered later compared to a non-mutant plant to isolate the SFT gene and study its function as a component of the mobile flowering signal "florigen" (Lifschitz, et al, 2006. ibid). However although this publication disclosed these sequences, their function of quantitatively modulating heterosis of yield-related traits when in the presence of a functional copy of the SFT gene (i.e. when in a heterozygous condition), was not disclosed previously.

The mutation in sft-stop is a single base-pair change at position 148 (from c to t) that causes an early stop codon that truncates the last two-thirds of the SFT protein. This mutation and its function are disclosed in the present application for the first time.

When in homozygous form, all three mutations cause similar phenotypic changes in the plant flowering time as described previously (Lifschitez et al, 2006. ibid). These changes result in agronomically inferior plants relative to normal plants not carrying the mutation due to loss of sympodial growth, extreme vegetative growth, and reduced yield. The present invention now discloses that when in heterozygous form these mutations lead to improvement in yield, as exemplified hereinbelow. Without wishing to be bound by any specific theory or mechanism of action, the heterotic phenotypic effect may be attributed to overdominance (ODO), wherein a synergistic superior performance of the heterozygous alleles located at the same locus is shown.

Thus, according to certain aspects, the present invention provides an isolated polynucleotide encoding a mutated sft protein having the amino acid sequence set forth in SEQ ID NO:3. According to certain embodiments, the polynucleotide comprises the nucleic acid sequence set forth in SEQ ID NO:4.

According to another aspect, the present invention provides a mutant parent inbred plant identified by the method of the present invention, the mutant parent inbred line conferring at least one heterosis-related phenotype to a hybrid offspring.

According to certain embodiments, the parent inbred line is homozygous for the mutant sft gene comprising the nucleic acid sequence set forth in SEQ ID NO:4.

According to a further aspect, the present invention provides a method for producing hybrid plant showing at least one heterotic phenotype, comprising:
a) providing a mutant parent inbred plant identified by the method of the present invention, homozygous for a single mutation in a single gene;
b) providing a non-mutant parent inbred plant, homozygous for wild type copies of the gene; and
c) crossing (hybridizing) the mutant parent inbred line with the non-mutant parent line;

thereby producing heterozygous hybrid plants showing at least one heterotic phenotype that is superior compared to the phenotypic performance of at least one the parent plants.

According to certain embodiments, the hybrid plant shows at least one heterotic phenotype that is superior compared to the phenotypic performance of the best parent plant.

According to certain embodiment, the gene is the tomato SFT gene or an ortholog thereof. According to these embodiments, the heterozygous hybrid plant comprises a structurally intact and functional wild-type SFT gene copy and a mutated sft copy, wherein the mutation in the sft copy is such that it reduces SFT gene function when homozygous; said heterozygous plant features a quantitative heterosis in respect to at least one yield related parameter as compared to a homozygous plant having two functional wild-type copies of the SFT gene.

According to certain embodiments, the wild type SFT gene encodes a protein having the amino acid sequence set for the in SEQ ID NO:1. According to one embodiment, the wild type SFT gene comprises a nucleic acid sequence as ser forth in SEQ ID NO:2.

According to other embodiments, the mutated sft gene encodes a protein having an amino acid sequence selected from the group consisting of SEQ ID NO:3; SEQ ID NO:5 and SEQ ID NO:7. According to additional embodiments, the mutated gene comprises a nucleic acid sequence selected from the group consisting of as SEQ ID NO:4; SEQ ID NO:6 and SEQ ID NO:8.

According to certain embodiments, the plant is tomato plant. According to other embodiments, the plant is a crop plant other then tomato and the gene is an ortholog of the SFT gene.

Hybrid plants produced by the method of the present invention are also encompassed within the scope of the present invention.

According to certain embodiments, the present invention provides a heterozygous hybrid plant comprising a structurally intact and functional wild-type SFT gene copy and a mutant sft copy, wherein the mutation in the sft copy is such that it reduces SFT gene function when homozygous; wherein the heterozygous plant shows a quantitative heterosis in respect to at least one yield related parameter as compared to a homozygous plant having two functional wild-type copies of the SFT gene.

According to certain typical embodiments, the present invention provide a hybrid plant heterozygous for the SFT gene, comprising a wild type SFT gene having the nucleic acid sequence set forth in SEQ ID NO:2 and a mutant sft gene having a nucleic acid sequence set forth in any one of SEQ ID NO:4, SEQ ID NO:6 and SEQ ID NO:8, wherein the hybrid plant has increased yield compared to a plant selected from the group consisting of a homozygous for the SFT gene and a plant homozygous for the sft gene.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

Identifying Mutant Inbred Plants Providing Heterosis-Related Phenotype

The crop plant tomato (*Solanum lycopersicum*) was first used to identify mutant inbred parent plants that confer at least one heterosis-related trait to a hybrid offspring. An inventor of the present invention and co-workers has previously generated an isogenic tomato "mutation library" in the genetic background of the processing tomato inbred variety M82 (Menda N Y et al., 2004. Plant J 38, 861-72). A total of 13,000 M2 families, derived from ethyl methane sulfonate (EMS) chemical treatment and fast-neutron mutagenesis of seeds, were phenotyped in field conditions and categorized into a morphological catalog that included 15 primary and 48 secondary categories. More than 3000 mutations have been identified, some of which represent new alleles of previously described phenotypes from the monogenic mutant collection of The Tomato Genetics Resource Center. Many mutations fall into more than a single category, and therefore have pleiotropic effects on plant growth. Mutants are searchable and accessed in the Solanaceae Genome Network (SGN) on a site called 'The Genes That Make Tomatoes'.

Figure 2:
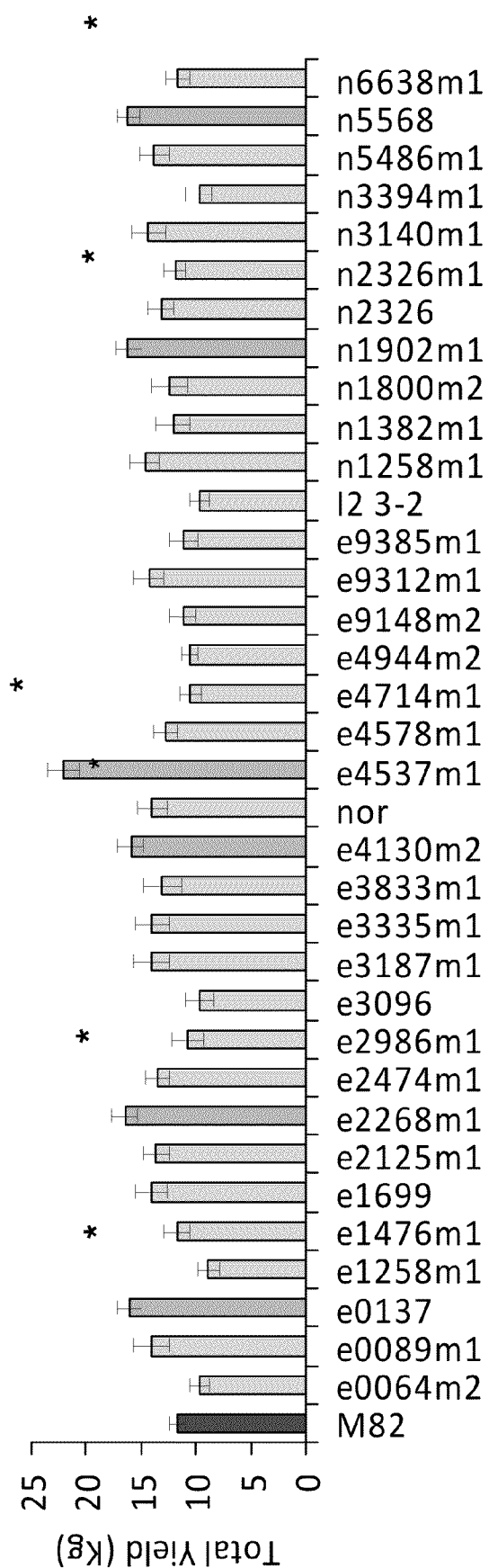
FIG. 2 shows total yield of hybrid plants heterozygous for an induced mutation. Hybrid plant showing significantly higher total yield compared to the M82 parent are marked with asterisks.

From this database, 35 individual single gene mutants affecting various categories of plant growth were selected for mutant hybrid evaluation by backcrossing to the inbred variety M82. The non-mutagenized inbred variety M82, and homozygous mutants served as control. Fifteen replicates from all mutant heterozygotes were planted in a randomized block design in agricultural field conditions (Akko, Israel). At maturity (~80-100% ripe (red) fruit), plants were harvested and measured for the following yield-related traits: 1. Plant weight; 2. Green fruit weight; 3. Red fruit weight; 4. Total yield; 5. Single fruit weight; 6. Total fruit number. Data were collected from 12 replicates for each genotype and compared statistically using the program JMP 6.0. In all cases, the yields from homozygous mutants were equal to M82 or significantly lower. Six mutant heterozygotes showed statistically significant higher yields than M82 ($p<0.05$; students t-test): e0137; e2268m1; e4130 m2; e4537m1; n1902m1; and n5568 (FIG. 2). The individual effects ranged from 15-87%.

This example illustrates that heterosis can be achieved from a single gene when one copy (allele) is mutated despite the remaining genes and intergenic chromosomal segments remaining by all practical considerations homozygous for the M82 genotype. The parent plants of the above-described heterozygotes can thus be used for breeding hybrid plants with increased yield.

Example 2

Identifying Heterosis-Related Mutations

The "mutation library" described above and the identified six mutants showing heterosis effects were used for identifying particular mutations that confer heterosis when in heterozygous form.

Figure 3A:
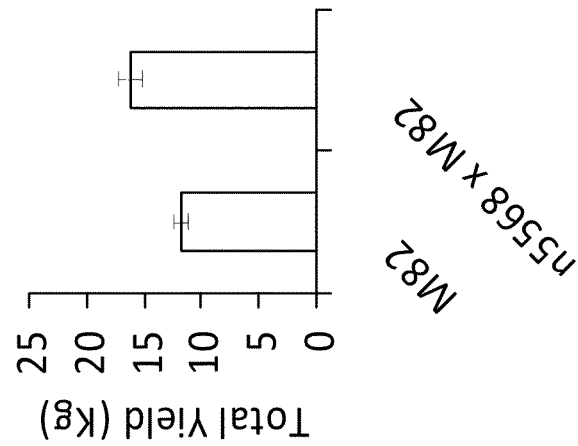
FIG. 3 shows heterosis for yield caused by heterozygosity for the sft-e4537 mutation (FIG. 3A), and heterozygosity in a second mutation called n5568 (FIG. 3B).
Figure 3B:
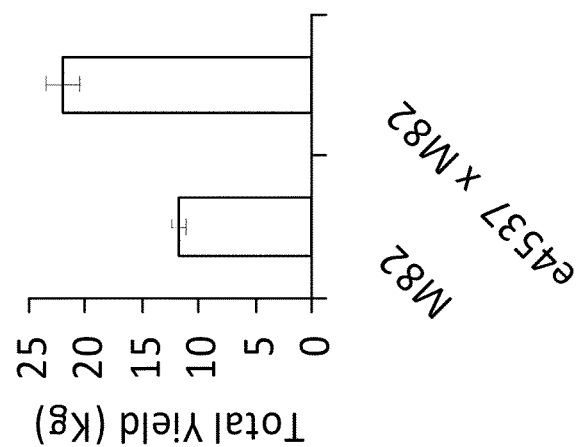

Among these six mutant hybrids, the mutant heterozygotes sft-e4537/+ and s-n5568/+ displayed the strongest overdominant effects (87% and 39% higher yield than the best parent, respectively, FIG. 3). The overdominant effect was attributed to heterozygosity with mutations in genes encoding the *Arabidopsis* orthologs of FT (tomato SFT) and WOX9, respectively.

The SFT gene was previously identified and shown to encode a protein that functions as a major component of florigen (Lifschitz et al., 2006. ibid). The sft-4537 heterozygous plant showed the strongest heterosis effects on total yield, as well as on multiple yield-related traits suggesting a dramatic pleiotropic effect on growth. The heterosis effects of the heterozygous sft-4537 mutant were reproducible in a second experimental environment in Kefar Masarik, Israel (Table 1).

TABLE 1

Single gene heterosis of tomato sft mutant heterozygote

| Genotype | Plant Weight (kg) | Green Fruit Weight (Kg) | Red Fruit Weight (Kg) | Total Yield (Kg) | Single Fruit Weight (g) | Fruit Number |
|---|---|---|---|---|---|---|
| LOCATION 1 AKKO | | | | | | |
| M82 | 3.87 (0.23) | 3.56 (0.41) | 8.10 (0.57) | 11.76 (0.76) | 66.3 (1.23) | 172.8 (10.46) |
| sft-4537 heterozygous plants | 5.77* (0.39) | 7.89* (0.71) | 14.19* (0.57) | 22.10* (1.3) | 78.7* (1.85) | 280.9* (15.78) |
| LOCATION 2 KEFAR MASARIK | | | | | | |
| M82 | 1.96 (0.23) | 1.13 (0.31) | 10.4 (0.91) | 11.53 (0.94) | 67.40 (3.1) | 173.9 (19.34) |
| sft-4537 heterozygous plants | 2.72* (0.23) | 1.43 (0.31) | 15.51* (0.91) | 16.94* (0.94) | 72.40 (2.9) | 235.5* (18.23) |

In Akko, Israel, all six measured traits of plant heterozygous for sft were statistically higher (p<0.05; Dunnett's t-test) than control homozygous M82 plants (marked by *). In Kefar Masarik, Israel, four out of six traits, including total yield were statistically higher (p<0.05) than control homozygous M82 plants (*). Numbers in parentheses represent standard errors.

The dramatic result observed for the single mutant sft provided support that this gene is responsible for the heterosis, but other explanations were possible (e.g. unknown background mutations or general mutagenesis induced regulatory changes). In order to obtain unequivocal evidence that heterozygosity of sft mutant alleles causes heterosis, three independently derived alleles of sft that resulted from a base substitution, deletion, and a stop codon in the gene of M82 were examined in the following year (2009).

The sft-4537 mutation described above is a single base-pair change that results in a single amino acid change from Threonine (T) to Isoleucine (I). sft-4537 is depicted in the nucleic acid sequence of SEQ ID NO:6, encoding a protein comprising the amino acid sequence set forth in SEX ID NO:5.

The sft-7187 mutation is a two base-pair deletion that causes a frame-shift and a downstream stop codon that truncates the C-terminus of the SFT protein. sft-7187 is depicted in the nucleic acid sequence of SEQ ID NO:8, encoding a protein comprising the amino acid sequence set forth in SEX ID NO:7. These two mutations were previously described (Lifschitz, et al, 2006, ibid)

The sft-stop mutation in is a single base-pair change that causes an early stop codon that truncates the last two-thirds of the SFT protein. sft-stop is depicted in the nucleic acid sequence of SEQ ID NO:4, encoding a protein comprising the amino acid sequence set forth in SEX ID NO:3.

This mutation is disclosed in this application for the first time so both the sequence per se and its lack of function are new.

Figure 4:
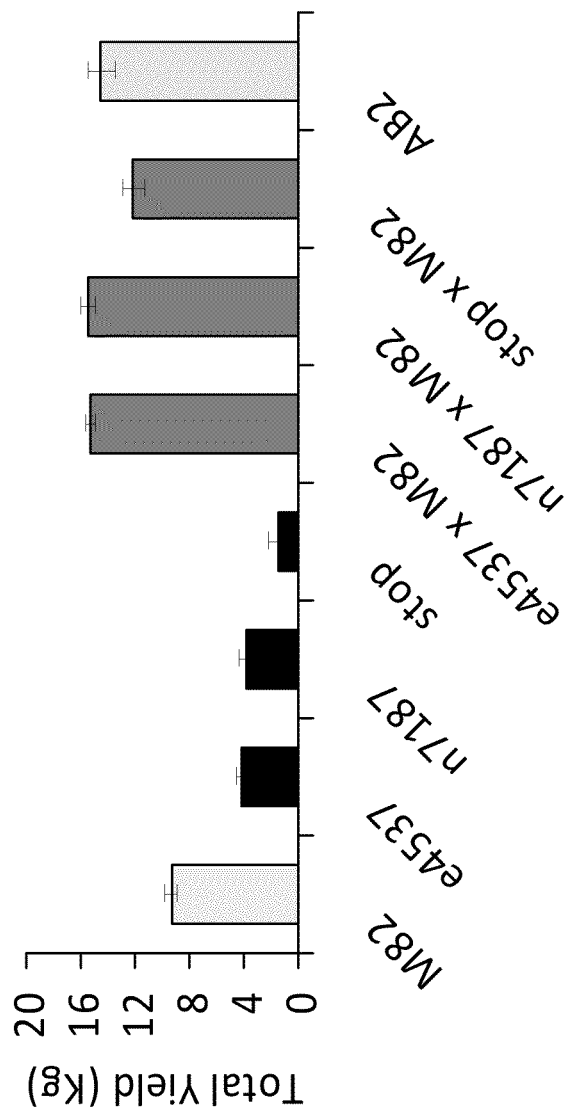
FIG. 4 shows heterosis for total fruit yield caused by heterozygosity for the sft-e4537, sft-n7187 and sft-stop in M82 background compared to M82, the parental homozygous mutant lines and the commercial hybrid AB 2.

All three alleles were crossed to M82 and the plants were tested in replicated trials in wide spacing (1 plant per m$^2$). As can be seen in FIG. 4, fruit yield of all three homozygous mutations was considerably lower than M82, revealing inbreeding depression, but all mutant hybrids had higher yield than M82 that nearly matched the leading commercial processing tomato hybrid AB2.

Figures 5A, 5B:
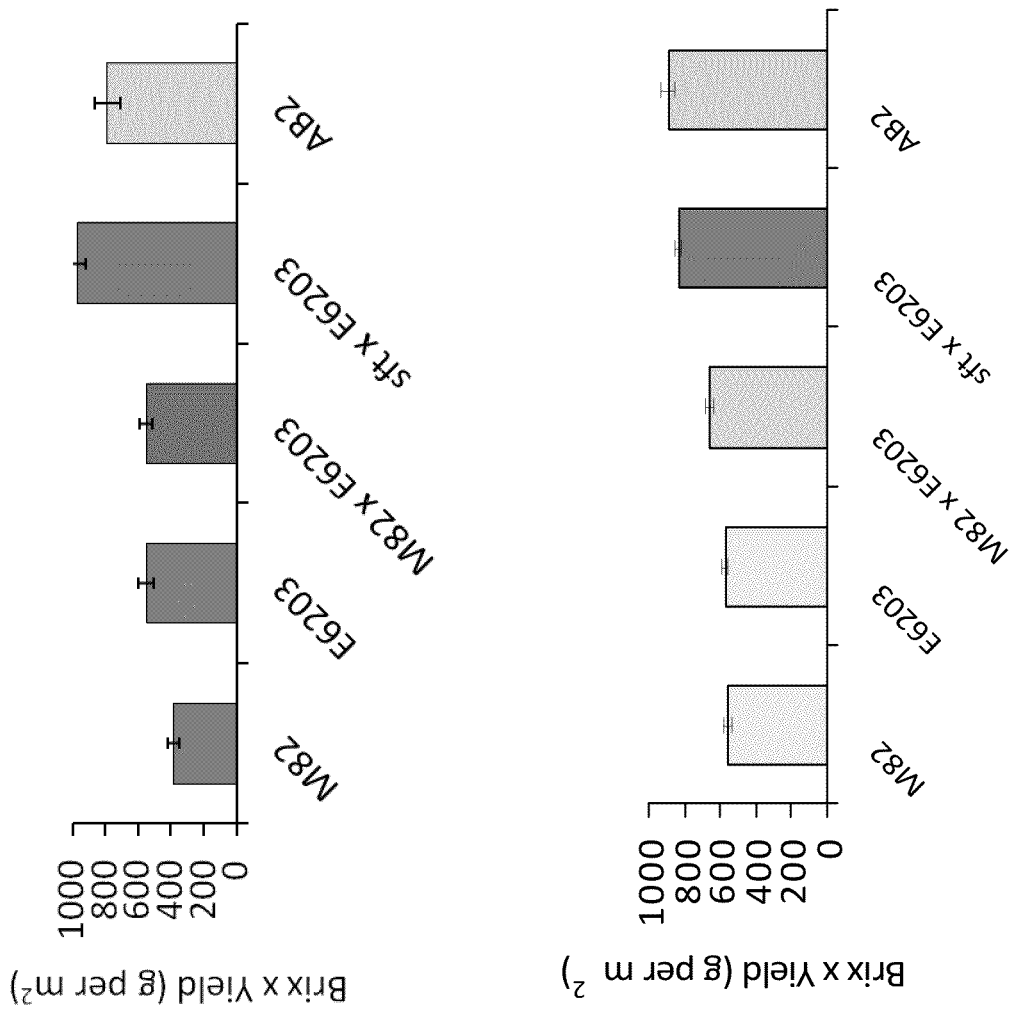
FIG. 5 shows comparison of Brix-Yield (g per m$^2$) of the isogenic hybrids M82×E6203 and M82sft×E6203 in wide (FIG. 5A) and dense spacing (FIG. 5B) compared to the parental lines and the commercial hybrid AB2.

Another test of the mutant ODO effect is to cross the mutants to another genetic background and generate hybrids with and without the variant sft alleles. M82 was crossed to E6203 (both lines are ~40 years old) and the F1 hybrid had sugar yield (g per m$^2$) similar to that of the inbred E6203. The hybrid of M82 that harbors the mutant allele with E6203 was significantly higher than the control hybrid in wide and dense spacing (FIGS. 5B and C) and similar to that of the modern high-yielding hybrid AB2. Similar results (data not shown) were obtained in different genetic backgrounds, planting density and drought conditions, thereby highlighting the power of the ODO effect of the sft mutation in various genetic backgrounds.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for producing an angiosperm hybrid plant showing at least one yield-related heterotic phenotype, comprising:

a. providing a mutant parent inbred angiosperm plant comprising a single mutation in a SINGLE FLOWER TRUSS (SFT) gene, wherein the mutation is such that it reduces SFT gene function when homozygous;

b. providing a parent inbred angiosperm plant, homozygous for wild-type alleles of the SFT gene, the wild-type gene encoding a protein having the amino acid sequence set forth in SEQ ID NO:1; and c. crossing the mutant parent inbred angiosperm plant with the parent inbred angiosperm plant, homozygous for wild-type alleles of said SFT gene;

thereby producing a heterozygous hybrid angiosperm plant comprising said wild-type SET allele and a mutated sft allele, wherein the heterozygous hybrid angiosperm plant shows at least one yield-related heterotic phenotype that is superior compared to a homozygous angiosperm plant having two wild-type alleles of said SFT gene.

2. The method of claim 1, wherein the parent inbred angiosperm plant, homozygous for wild-type alleles of the gene, is isogenic to the mutant parent inbred angiosperm plant.

3. The method of claim 1, wherein the wild-type SFT gene comprises the nucleic acid sequence as set forth in SEQ ID NO:2.

4. The method of claim 1, wherein the mutated sft gene encodes a protein having the amino acid sequence set forth in SEQ ID NO:3.

5. The method of claim 4, wherein the mutated sft gene comprises the nucleic acid sequence as set forth in SEQ ID NO:4.

6. The method of claim 1, wherein the angiosperm plant is a *Solanum lycopersicum* plant.

7. A hybrid angiosperm plant produced according to the method of claim 1.

8. The method of claim 1, wherein the mutated sft gene encodes a protein having the amino acid sequence set forth in SEQ ID NO:5.

9. The method of claim 1, wherein the mutated sft gene encodes a protein having the amino acid sequence set forth in SEQ ID NO:7.

10. The method of claim 8, wherein the mutated sft gene comprises the nucleic acid sequence as set forth in SEQ ID NO:6.

11. The method of claim 9, wherein the mutated sft gene comprises the nucleic acid sequence as set forth in SEQ ID NO:8.

12. A hybrid angiosperm plant comprising a wild-type SFT allele having the nucleic acid sequence set forth in SEQ ID NO:2 and a mutated sft allele having the nucleic acid sequence set forth in any one of SEQ ID NO:4, SEQ ID NO:6, and SEQ ID NO:8 wherein the mutation in the sft allele is such that it reduces SFT gene function when homozygous, and wherein said hybrid angiosperm plant shows at least one heterotic yield phenotype compared to a homozygous angiosperm plant having two wild-type alleles of the SET gene.

13. The hybrid angiosperm plant of claim 12, wherein the mutant sft gene comprises a nucleic acid sequence as set forth in SEQ ID NO:4.

* * * * *

SEQUENCE LISTING

```
<160> NUMBER OF SEQ ID NOS: 8

<210> SEQ ID NO 1
<211> LENGTH: 175
<212> TYPE: PRT
<213> ORGANISM: Lycopersicon esculentum

<400> SEQUENCE: 1

Met Pro Arg Glu Arg Asp Pro Leu Val Gly Arg Val Val Gly Asp
1               5                   10                  15

Leu Asp Pro Phe Thr Arg Thr Ile Gly Leu Arg Val Ile Tyr Arg Asp
                20                  25                  30

Arg Glu Val Asn Asn Gly Cys Glu Leu Arg Pro Ser Gln Val Ile Asn
            35                  40                  45

Gln Pro Arg Val Glu Val Gly Gly Asp Asp Leu Arg Thr Phe Phe Thr
        50                  55                  60
```

```
Leu Met Val Asp Pro Asp Ala Pro Ser Pro Ser Asp Pro Asn Leu Arg
 65                  70                  75                  80

Glu Tyr Leu His Trp Leu Val Thr Asp Ile Pro Ala Thr Thr Gly Ser
                 85                  90                  95

Ser Phe Gly Gln Glu Ile Val Ser Tyr Glu Ser Pro Arg Pro Ser Met
            100                 105                 110

Gly Ile His Arg Phe Val Phe Val Leu Phe Arg Gln Leu Gly Arg Gln
            115                 120                 125

Thr Val Tyr Ala Pro Gly Trp Arg Gln Asn Phe Asn Thr Arg Asp Phe
        130                 135                 140

Ala Glu Leu Tyr Asn Leu Gly Leu Pro Val Ala Val Tyr Phe Asn
145                 150                 155                 160

Cys Gln Arg Glu Ser Gly Ser Gly Arg Arg Ser Ala Asp
                165                 170                 175

<210> SEQ ID NO 2
<211> LENGTH: 534
<212> TYPE: DNA
<213> ORGANISM: Lycopersicon esculentum

<400> SEQUENCE: 2
atgcctagag aacgtgatcc tcttgttgtt ggtcgtgtgg tagggatgt attggaccct      60 ttcacaagaa ctattggcct aagagttata tatagagata gagaagttaa taatggatgc   120
gagcttaggc cttcccaagt tattaaccag ccaaggggttg aagttggagg agatgaccta  180
cgtacctttt tcactttggt tatggtggac cctgatgctc aagtccgag tgatccaaat   240 ctgagagaat accttcactg gttggtcacc gatattccag ctaccacagg ttcaagtttt   300
gggcaagaaa tagtgagcta tgaaagtcca agaccatcaa tgggaataca tcgatttgta   360
tttgtattat tcagacaatt aggtcggcaa acagtgtatg ctccaggatg gcgtcagaat   420
ttcaacacaa gagattttgc agaactttat aatcttggtt tacctgttgc tgctgtctat   480
tttaattgtc aaagagagag tggcagtggt ggacgtagaa gatctgctga ttga          534

<210> SEQ ID NO 3
<211> LENGTH: 49
<212> TYPE: PRT
<213> ORGANISM: Artificial Sequence
<220> FEATURE:
<223> OTHER INFORMATION: Synthetic polypeptide; sft mutant

<400> SEQUENCE: 3

Met Pro Arg Glu Arg Asp Pro Leu Val Val Gly Arg Val Val Gly Asp
 1               5                  10                  15

Val Leu Asp Pro Phe Thr Arg Thr Ile Gly Leu Arg Val Ile Tyr Arg
                20                  25                  30

Asp Arg Glu Val Asn Asn Gly Cys Glu Leu Arg Pro Ser Gln Val Ile
            35                  40                  45

Asn

<210> SEQ ID NO 4
<211> LENGTH: 534
<212> TYPE: DNA
<213> ORGANISM: Artificial Sequence
<220> FEATURE:
<223> OTHER INFORMATION: Synthetic polynucleotide; sft mutant

<400> SEQUENCE: 4
atgcctagag aacgtgatcc tcttgttgtt ggtcgtgtgg tagggatgt attggaccct      60
```

```
ttcacaagaa ctattggcct aagagttata tatagagata gagaagttaa taatggatgc    120
gagcttaggc cttcccaagt tattaactag ccaagggttg aagttggagg agatgaccta    180 cgtaccttt tcactttggt tatggtggac cctgatgctc caagtccgag tgatccaaat     240
ctgagagaat accttcactg gttggtcacc gatattccag ctaccacagg ttcaagtttt    300
gggcaagaaa tagtgagcta tgaaagtcca agaccatcaa tgggaataca tcgatttgta    360
tttgtattat tcagacaatt aggtcggcaa acagtgtatg ctccaggatg gcgtcagaat    420
ttcaacacaa gagattttgc agaactttat aatcttggtt tacctgttgc tgctgtctat    480
tttaattgtc aaagagagag tggcagtggt ggacgtagaa gatctgctga ttga          534
```

<210> SEQ ID NO 5
<211> LENGTH: 175
<212> TYPE: PRT
<213> ORGANISM: Artificial Sequence
<220> FEATURE:
<223> OTHER INFORMATION: Synthetic polypeptide; sft mutant

<400> SEQUENCE: 5

```
Met Pro Arg Glu Arg Asp Pro Leu Val Val Gly Arg Val Val Gly Asp
1               5                   10                  15

Leu Asp Pro Phe Thr Arg Thr Ile Gly Leu Arg Val Ile Tyr Arg Asp
                20                  25                  30

Arg Glu Val Asn Asn Gly Cys Glu Leu Arg Pro Ser Gln Val Ile Asn
            35                  40                  45

Gln Pro Arg Val Glu Val Gly Gly Asp Asp Leu Arg Thr Phe Phe Ile
        50                  55                  60

Leu Met Val Asp Pro Asp Ala Pro Ser Pro Ser Asp Pro Asn Leu Arg
65                  70                  75                  80

Glu Tyr Leu His Trp Leu Val Thr Asp Ile Pro Ala Thr Thr Gly Ser
                85                  90                  95

Ser Phe Gly Gln Glu Ile Val Ser Tyr Glu Ser Pro Arg Pro Ser Met
                100                 105                 110

Gly Ile His Arg Phe Val Phe Val Leu Phe Arg Gln Leu Gly Arg Gln
            115                 120                 125

Thr Val Tyr Ala Pro Gly Trp Arg Gln Asn Phe Asn Thr Arg Asp Phe
        130                 135                 140

Ala Glu Leu Tyr Asn Leu Gly Leu Pro Val Ala Ala Val Tyr Phe Asn
145                 150                 155                 160

Cys Gln Arg Glu Ser Gly Ser Gly Gly Arg Arg Ser Ala Asp
                165                 170                 175
```

<210> SEQ ID NO 6
<211> LENGTH: 534
<212> TYPE: DNA
<213> ORGANISM: Artificial Sequence
<220> FEATURE:
<223> OTHER INFORMATION: Synthetic polynucleotide; sft mutant

<400> SEQUENCE: 6

```
atgcctagag aacgtgatcc tcttgttgtt ggtcgtgtgg tagggatgt attggaccct      60 ttcacaagaa ctattggcct aagagttata tatagagata gagaagttaa taatggatgc    120
gagcttaggc cttcccaagt tattaaccag ccaagggttg aagttggagg agatgaccta    180 cgtaccttt tcattttggt tatggtggac cctgatgctc caagtccgag tgatccaaat     240
ctgagagaat accttcactg gttggtcacc gatattccag ctaccacagg ttcaagtttt    300
```

```
gggcaagaaa tagtgagcta tgaaagtcca agaccatcaa tgggaataca tcgatttgta    360
tttgtattat tcagacaatt aggtcggcaa acagtgtatg ctccaggatg gcgtcagaat    420
ttcaacacaa gagattttgc agaactttat aatcttggtt tacctgttgc tgctgtctat    480
tttaattgtc aaagagagag tggcagtggt ggacgtagaa gatctgctga ttga          534

<210> SEQ ID NO 7
<211> LENGTH: 143
<212> TYPE: PRT
<213> ORGANISM: Artificial Sequence
<220> FEATURE:
<223> OTHER INFORMATION: Synthetic polypeptide; sft mutant

<400> SEQUENCE: 7

Met Pro Arg Glu Arg Asp Pro Leu Val Val Gly Arg Val Gly Asp
1               5                   10                  15

Val Leu Asp Pro Phe Thr Arg Thr Ile Gly Leu Arg Val Ile Tyr Arg
            20                  25                  30

Asp Arg Glu Val Asn Asn Gly Cys Glu Leu Arg Pro Ser Gln Val Ile
        35                  40                  45

Asn Gln Pro Arg Val Glu Val Gly Gly Asp Asp Leu Arg Thr Phe Phe
    50                  55                  60

Thr Leu Val Met Val Asp Pro Asp Ala Pro Ser Pro Ser Asp Pro Asn
65                  70                  75                  80

Leu Arg Glu Tyr Leu His Trp Leu Val Thr Asp Ile Pro Ala Thr Thr
                85                  90                  95

Gly Ser Ser Phe Gly Gln Glu Ile Val Ser Tyr Glu Ser Pro Arg Pro
            100                 105                 110

Ser Met Gly Ile His Arg Phe Val Phe Val Leu Phe Arg Gln Leu Gly
        115                 120                 125

Arg Gln Thr Val Tyr Asn Leu Gly Leu Pro Cys Cys Cys Leu Phe
    130                 135                 140

<210> SEQ ID NO 8
<211> LENGTH: 532
<212> TYPE: DNA
<213> ORGANISM: Artificial Sequence
<220> FEATURE:
<223> OTHER INFORMATION: Synthetic polynucleotide; sft mutant

<400> SEQUENCE: 8
atgcctagag aacgtgatcc tcttgttgtt ggtcgtgtgg tagggdatgt attggaccct    60
ttcacaagaa ctattggcct aagagttata tatagagata gagaagttaa taatggatgc    120
gagcttaggc cttcccaagt tattaaccag ccaaggggttg aagttggagg agatgaccta   180
cgtacctttt tcactttggt tatggtggac cctgatgctc caagtccgag tgatccaaat    240
ctgagagaat accttcactg gttggtcacc gatattccag ctaccacagg ttcaagtttt    300
gggcaagaaa tagtgagcta tgaaagtcca agaccatcaa tgggaataca tcgatttgta    360
tttgtattat tcagacaatt aggtcggcaa acagtgtatg ctccaggatg gcgtcagaat    420
ttcaacacaa gagattttgc agaactttat aatcttggtt taccttgctg ctgtctattt    480
taattgtcaa agagagagtg gcagtggtgg acgtagaaga tctgctgatt ga            532
```